United States Patent [19]

Lindmayer

[11] Patent Number: 5,190,523

[45] Date of Patent: Mar. 2, 1993

[54] DISPOSABLE SYRINGE AND INJECTOR

[75] Inventor: Istvan Lindmayer, Pierrefonds, Canada

[73] Assignee: Idee International R & D Inc., Montreal, Canada

[21] Appl. No.: 746,340

[22] Filed: Aug. 16, 1991

[51] Int. Cl.⁵ .................................. A61M 5/30
[52] U.S. Cl. .................................. 604/72; 604/68; 604/222
[58] Field of Search .................. 604/68–72, 604/218, 221, 222, 236–238; 222/386

[56] References Cited

U.S. PATENT DOCUMENTS

| | | | |
|---|---|---|---|
| 3,859,996 | 1/1975 | Mizzy et al. | 604/71 |
| 4,059,107 | 11/1977 | Iriguchi et al. | 604/71 |
| 4,941,880 | 7/1990 | Burns | 604/70 |
| 5,062,830 | 11/1991 | Dunlap | 604/72 |
| 5,064,413 | 11/1991 | McKinnon et al. | 604/72 |

FOREIGN PATENT DOCUMENTS

| | | | |
|---|---|---|---|
| 17315 | 4/1934 | Australia | 222/386 |
| 1115773 | 3/1958 | France | 604/218 |

Primary Examiner—Stephen C. Pellegrino
Assistant Examiner—Ralph A. Lewis
Attorney, Agent, or Firm—George A. Seaby

[57] ABSTRACT

In general, syringes for needleless injectors must be resonably accurately dimensioned, and the barrel of the injector must be formed of metal in order to prevent expansion of the syringe under pressure. A simple alternative is a syringe including an elongated tubular body with one open end and a closed end containing an injection orifice, and a plug slidable in the body with a prong at one end of the plug extending towards the orifice end of the body, the prong carrying an O-ring and an annular seal which prevents squeezing of the O-ring between the body of the syringe and the plug under injection pressures. An alternative form of syringe includes a pair of valves, one of which normally closes the injection orifice, and the other of which is mounted on the plug. the orifice valve opens under injection pressure to permit the passage of medicine from the syringe body through the orifice, and the other valve opens when the plug, which contains a longitudinally extending passage, is moved away from the orifice end of the syringe body. With such syringes, the body of the injector can be manufactured from plastic, as can the barrel for receiving the syringe. Moreover parts no longer need to be particularly accurately dimensioned.

7 Claims, 5 Drawing Sheets

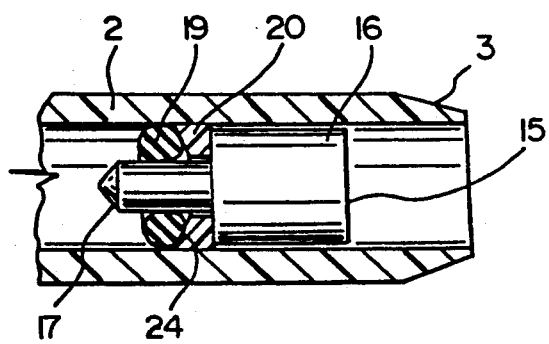
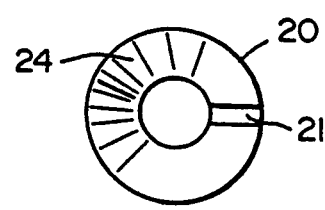
FIG. 3
FIG. 4
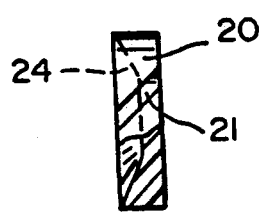
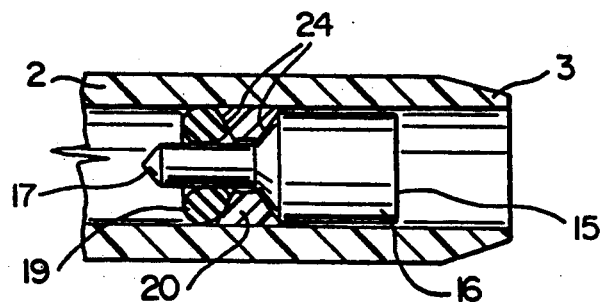
FIG. 5
FIG. 6

DISPOSABLE SYRINGE AND INJECTOR

BACKGROUND OF THE INVENTION

1. Field of the Invention

This invention relates to a syringe, and to a needleless injector for use with the syringe.

2. DISCUSSION OF THE PRIOR ART

The present inventor has been involved in the field of needleless injectors for many years, his name appearing in many patents, including Canadian Patents Nos. 1,178,503, issued on Nov. 27, 1984; 1,256,343, issued Jun. 27, 1989 and 1,258,019, issued Aug. 1, 1989, and U.S. Pat. Nos. 4,342,310, issued Aug. 3, 1982 and 4,518,385, issued May 21, 1985.

In general, needleless injectors of the type described in the above patents, and the vials or syringes used in the injectors must be carefully manufactured to close tolerances. Moreover, the injectors usually are produced from stainless steel, which prevents the expansion of the plastic syringes containing the medicine. Consequently, the cost of material and production is substantial, and a need exists for a less expensive alternative.

GENERAL DESCRIPTION OF THE INVENTION

An object of the present invention is to meet the above defined need by providing a relatively simple syringe, which can be produced form plastic, and which need not be as accurately dimensioned as existing devices of the same type.

Another object of the invention is to provide a needleless injector, which can be produced mainly of plastic for use with the syringe of the present invention.

Accordingly, the present invention relates to a syringe for a needleless injector comprising tubular body means defining a medicine chamber, said body means having one closed end and an open end; orifice means in said closed end for discharging medicine from said chamber; plug means slidable in said chamber between said open and closed ends for pushing medicine through said orifice means; prong means extending inwardly from said plug means into said medicine chamber; 0-ring means on said prong means for creating a fluid-tight seal between said plug means and said body means; and sealing ring means on said prong means for preventing entry of said 0-ring means between said plug means and said body means during movement of said plug means towards said orifice means.

BRIEF DESCRIPTION OF THE DRAWINGS

The invention will be described in greater detail with reference to the accompanying drawings, which illustrate preferred embodiments of a syringe and needleless injector in accordance with the present invention, and wherein:

FIG. 3 is a longitudinal sectional view of the right-hand end of the syringe of FIGS. 1 and 2 on a larger scale;

FIG. 4 is an end elevational view of a split ring or washer used in the syringe of FIGS. 1 to 3 as seen from the left of FIG. 3;

FIG. 5 is a partly sectioned side elevational view of the washer of FIG. 4;

FIG. 6 is a longitudinal sectional view similar to FIG. 3, of an alternative embodiment of a split ring or washer for use in the syringe of FIGS. 1 and 2;

DESCRIPTION OF PREFERRED EMBODIMENT

Figure 1:
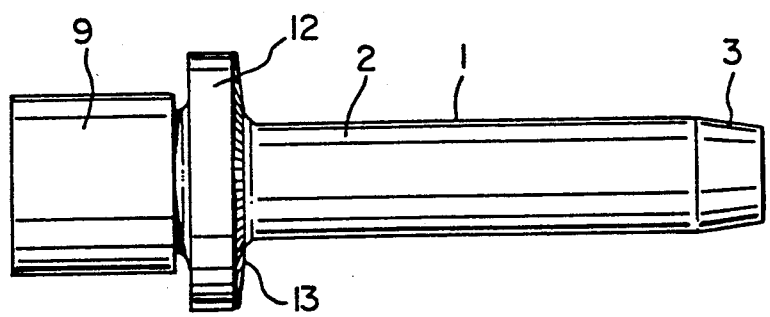
FIG. 1 is a side elevational view of a disposable syringe in accordance with the present invention.
Figure 2:
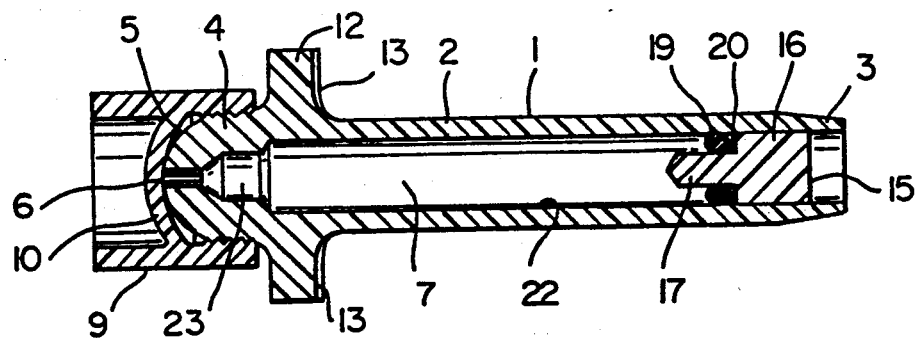
FIG. 2 is a longitudinal sectional view of the syringe of FIG. 1.

Referring to FIGS. 1 to 3, a disposable syringe 1 in accordance with the present invention includes an elongated, tubular cylindrical body or body 2 with a tapering open end 3 and a closed domed end defining a nozzle 4. The nozzle 4 includes a convex outer end 5 containing a central stainless steel insert defining an injection orifice 6 through which medicine can be discharged from a chamber 7 in the body 2. The cylindrical nozzle 4 is threaded for receiving a cylindrical cap or cover 9. The cover 9 includes a concavoconvex transversely extending partition 10, which closes the orifice 6 when the cover is screwed tightly onto the nozzle 4. An annular flange 12 extends outwardly from the body 2 rearwardly of the nozzle 4 for limiting movement of the syringe 1 into an needleless injector, as described hereinafter in greater detail. Radially extending sawtooth projections 13 are provided on the surface of the flange 12 opposite the nozzle 4 for preventing rotation of the body 2 in a needleless injector.

As mentioned above, the body 2 defines a medicine chamber 7. The chamber 7 is closed by a plug 15 which includes a cylindrical body 16 and a prong 17 extending into the medicine chamber 7. An 0-ring 19 and an annular seal or washer 20 are provided on the prong 17. The washer 20, which is in fact a split ring with a slot 21 (FIGS. 4 and 5), is designed to expand with the body 2 to prevent movement of the 0-ring 19 between the body 16 of the plug 15 and the interior surface 22 of the body 2 when the plug 15 is pushed towards the orifice 6 under pressure. The slot 21 is inclined with respect to the front and rear surfaces of the washer so that the 0-ring 19 cannot be squeezed into the slot. As the plug 15 moves towards the orifice 6, the prong 17 enters a reduced diameter portion 23 of the chamber 7 ensuring that virtually all of the medicine is expelled from the body 2. The orifice or front surface of the washer 20 is inclined inwardly, so that the pressure of the medicine in the syringe presses the 0-ring 19 against the washer 20 to force the latter outwardly against the interior surface 22 of the body 2. Alternatively, as best shown in FIG. 6, both surfaces 24 of the washer 20 can be bevelled inwardly, so that forces acting on either side force the washer outwardly against the interior 22 of the body 2.

Figure 7:
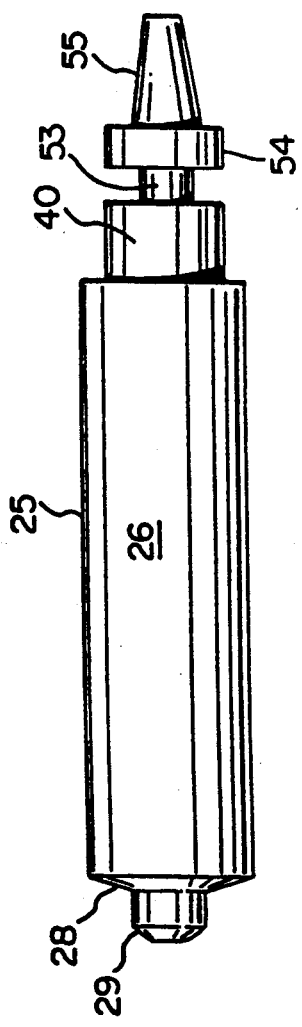
FIG. 7 is a side elevational view of a second embodiment of syringe in accordance with the present invention.
Figure 8:
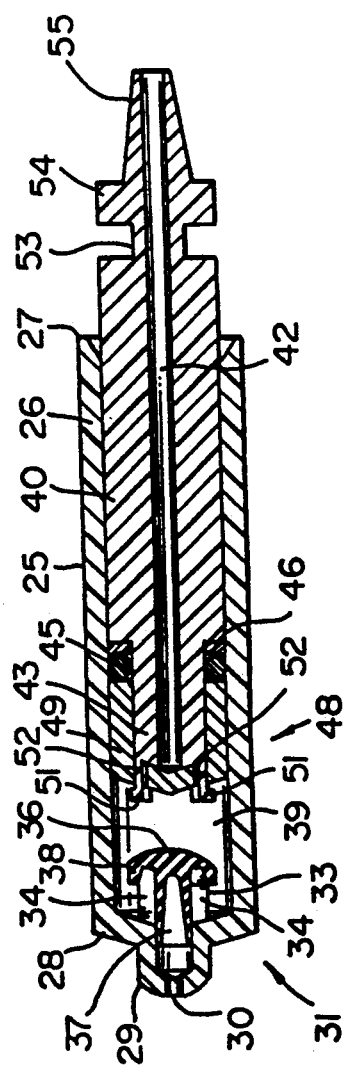
FIG. 8 is a longitudinal sectional view of the syringe of FIG. 7.

With reference to FIGS. 7 and 8, a second embodiment of the syringe 25 of the present invention includes an elongated tubular body or body 26 with an open end 27 and a closed end 28. A nozzle 29 with an injection orifice 30 therein extends outwardly from the closed end 28 of the body 26. The orifice 30 is normally closed by a valve generally indicated at 31. The valve 31 is defined by a short tube 33 extending inwardly away from the nozzle 29. Longitudinally extending slots 34 are provided in the top and bottom of the tube 33. A resilient rubber plug 36 extends into the tube 33. The plug 36 includes a tubular body 37 and an annular, domed head 38 extending around the open inner end of the tube 33. When liquid in the medicine chamber 39 is subjected to pressure by virtue of movement of a plug or plunger 40 towards the orifice 30, the medicine passes through the slots 34 pressing against the tubular body 37 of the valve 36 to open the valve permitting discharge of medicine through the orifice 30.

The plunger 40 is slidably mounted in the body 26. A central passage 42 is provided in the plunger 40 for admitting medicine into the medicine chamber 39. As in the case of the first embodiment of the invention, a prong 43 is provided on the inner end of the plug or plunger 40. An 0-ring 45 and an annular split ring or washer 46 are mounted on the prong 43. The 0-ring 45 and the seal 46 perform the same function as the 0-ring 19 and the washer 20, respectively of the first embodiment of the invention. The front or inner end of the passage 42 is closed by a second valve generally indicated at 48. The valve 48 includes a cylindrical cover 49 mounted on the prong 43. The cover 49 is retained on the prong 43 by generally L-shaped fingers 51 extending through openings 52 in the inner end of the cover 49. When the plunger 40 is withdrawn from the orifice end of the body 26, a partial vacuum is created in the medicine chamber 39, whereby the cover 49 is caused to slide on the prong 43 to an open position (not shown) against the outer ends of the fingers 51. Medicine is drawn through the passage 42 from a bag (not shown) and is admitted to the chamber 39 via the openings 52 in the cover 49. When the plug 40 moves towards the orifice 30, the cover 49 is pressed against the inner end of the passage 42 to close the latter.

An annular groove 53 is provided in the end of the plug 40 extending out of the body 26. The groove 53 is followed by a ring 54 and a tapering end 55 for connecting the syringe 25 to a source (not shown) of medicine.

Figure 9:
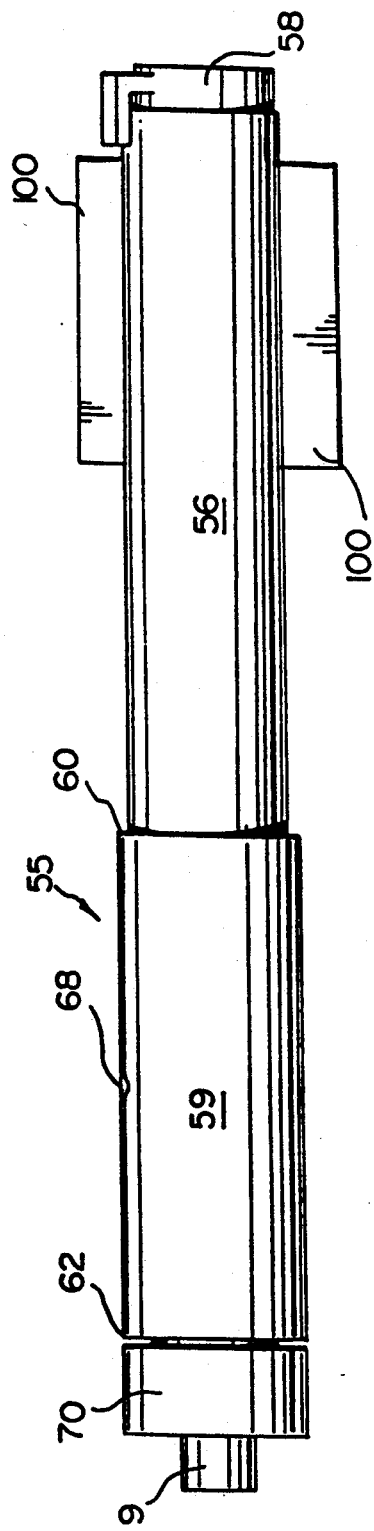
FIG. 9 is a side elevational view of an needleless injector utilizing the syringe of FIGS. 1 and 2.
Figure 10:
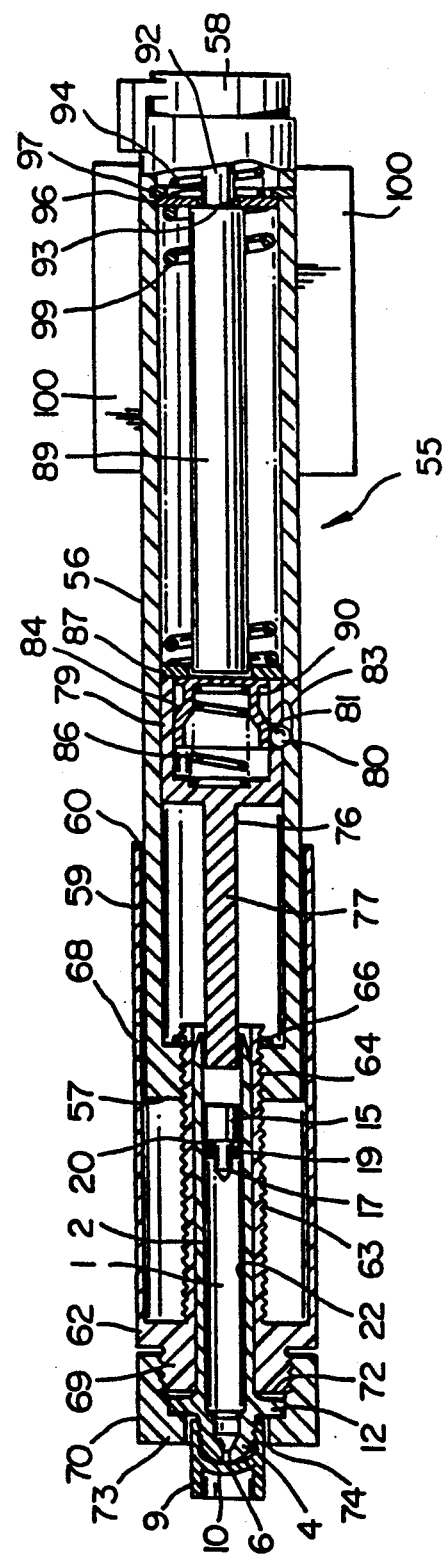
FIG. 10 is a longitudinal sectional view of the syringe of FIG. 9.

With reference to FIGS. 9 and 10, a needleless injector 55 for use with the syringe of FIGS. 1 and 2 includes a cylindrical casing 56, one end 57 of which is closed, and the other end of which is closed by a trigger or actuator button 58. A sleeve 59 is mounted on the closed end 57 of the casing 56. The sleeve 59 has an open end 60 and a closed end 62. An externally threaded cylinder or barrel 63 extends inwardly through the closed end 62 of the sleeve 59. The barrel 63 extends through a threaded opening 64 in the end 57 of the casing 56. Outward movement of the barrel 63, and consequently of the sleeve 59 is limited by a split ring 66 on the inner end of the barrel 63, i.e. the end of the barrel 63 in the casing 56. Rotation of the sleeve 59, and consequently of the barrel 63 causes movement of the barrel 63 into the casing 56. A window 68 is provided in the side of the sleeve 59 for observing indicia (not shown) on the casing 56 indicative of the dosage being administered using the injector.

A threaded neck 69, defining the front or outer end of the barrel 63, extends outwardly from the front end 62 of the sleeve 59 for receiving an internally threaded syringe cover 70. A prefilled syringe 1 is inserted into the neck 69, the front end 72 of which has raised extending sawtooth projections for mating with the projections 13 on the syringe. The cover 70 is placed on the neck 69, so that radially, inwardly extending flange 73 on the front end thereof bears against the flange 12 of the syringe 1 to retain the latter in the barrel 63. The opening 74 in the outer end of the cover 70 is sufficiently large to permit removal and replacement of the cover 9 from the nozzle 4 of the syringe 1. Movement of the plug 15 in the body 2 of the syringe 1 is effected by a plunger 76, which is slidably mounted in the casing 56. The plunger 76 includes an elongated rod 77 for insertion into the open trailing end 3 of the syringe body 2, and a cup-shaped bushing 79 integral with the rod 77 for sliding in the casing 56. The bushing 79 is maintained in a loaded position (FIG. 10) by a latch, which includes a ball 80 in an opening 81 in the side of the bushing 79. The ball 80 rests in a groove 83 in the interior of the casing 56. A cup-shaped collar 84 in the open rear end of the bushing 79 retains the ball in the groove 83. The collar 84 is biased to the loaded or latched position by a small helical spring 86. The collar 84 is retained in the bushing 79 by a ring 87.

An elongated plunger 89 is used to move the collar 84 into the bushing 79 so that the ball 80 can enter an annular recess 90 in the collar 84 permitting sliding of the bushing 79 in the casing 56. The plunger 89 includes a reduced diameter trailing end 92 and a shoulder 93. The plunger 89 is biased towards the button 58 by a small helical spring 94 bearing against a guide ring 96, which is retained in position by a split ring 97. The plunger 76 is moved towards the orifice end of the sleeve 59 by a helical spring 99. When the button 58 is pressed, the plunger 89 moves forwardly to move the collar 84 to the ball release position. When the ball 80 enters the annular groove 90, the bushing 79 is free to move forwardly, so that the rod 77 moves rapidly forwardly against the plug 15. With the cover 9 removed, sufficient pressure is generated that the drop of medicine discharged through the orifice 6 breaks the skin, so that the medicine can be injected. For such purpose, there is a gap between the trailing end of the plug 15 in the syringe 1 and the leading or front end of the plunger 76. Forward movement of the plunger 76 ceases when the bushing 79 hits the inner end of the barrel 63, at which point the plug 15 has reached the orifice end of the syringe.

The cover 70 is removed and the disposable syringe 1 is removed from the barrel 63. In order to reload the injector 55, the barrel 63 is wound into the end 57 of the casing 56 to push the bushing 79 rearwardly against the bias of the spring 99 until the ball 80 drops into the groove 83. The sleeve 59 is then rotated in the opposite direction until the desired setting is observed through the window 68, at which time a new disposable, prefilled syringe 1 is inserted into the barrel 63, and the injector can be again fired. The setting will determine the gap between the plug 15 and the plunger 76, and thus the depth of penetration of the medicine. The setting may require altering depending upon whether a human or an animal (e.g. pig, cow or horse) is being injected. A pair of wings 100 are provided on the actuator button end of the casing 56 for facilitating handling of the injector.

Figure 11:
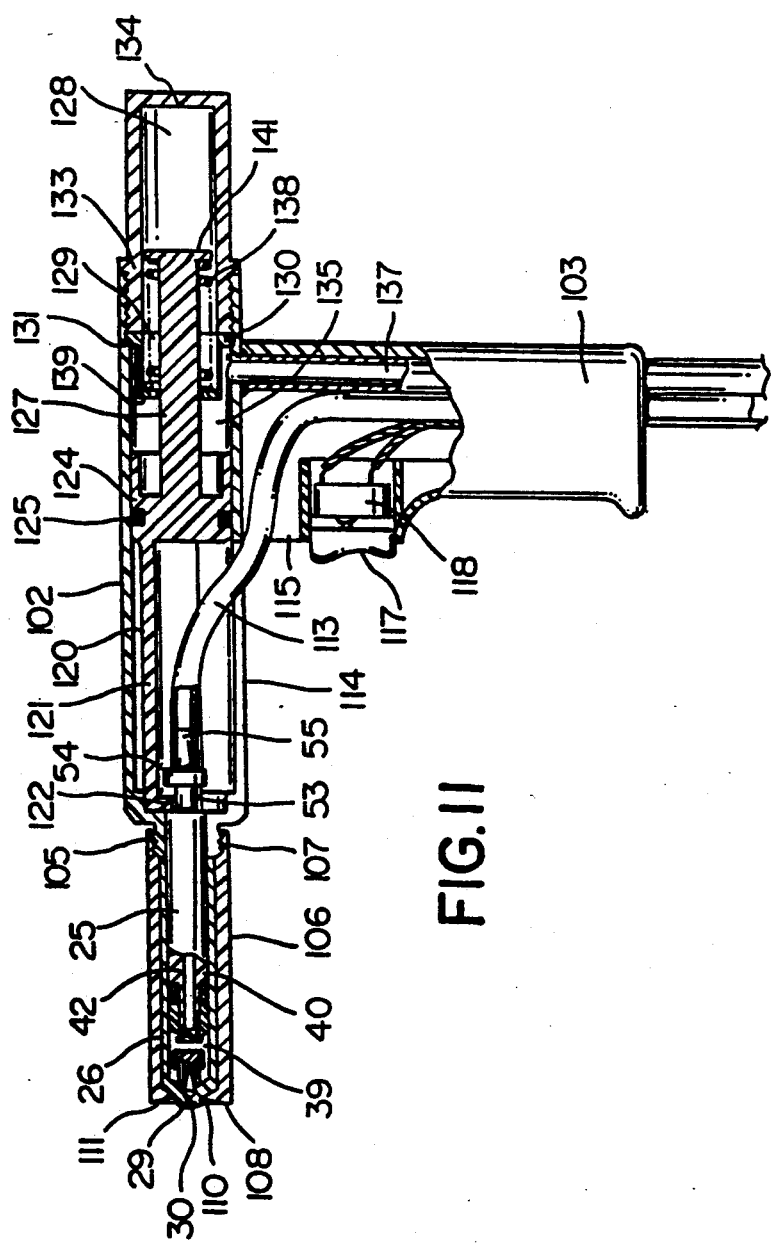
FIG. 11 is a longitudinal sectional view of a gun-type needleless injector utilizing the syringe of FIGS. 7 and 8.

Referring to FIG. 11, a pistol-type needleless injector using the refillable syringe 25 of FIGS. 7 and 8 includes an elongated cylindrical casing 102, with a hollow handle 103 perpendicular thereto. An externally threaded neck 105 extends forwardly from the front end of the casing 102 for receiving a tubular syringe 25 holder 106. For such purpose, one end 107 of the syringe holder 106 is internally threaded for engaging the neck 105. The other closed end 108 of the holder 106 engages the closed end 28 of the syringe body 26 for retaining the syringe in the holder 106. The nozzle 29 of the syringe 25 extends outwardly through an opening 110 in the otherwise closed end 111 of the holder 106. The inner, tapered end 55 of the syringe plug 40 is connected to a supply of medicine such as a plastic bag (not shown) by a tube 113, which extends through a slot 114 in the bottom center of the casing 102. The tube 113 extends through the slot 114, an opening 115 in the front of the handle 103 above a trigger 117 and downwardly through the handle to the bag of medicine. When the plug 40 is withdrawn from the casing 26 (moved to the right in FIG. 11) a partial vacuum is created in the chamber 39, whereby the valve 48 (FIG. 8) opens and medicine is drawn through the tube 113 and the passage 42 into the chamber 39 of the syringe 25. When the trigger 117 is depressed to close a switch 118, hydraulic fluid is introduced into the injector as described hereinafter in greater detail.

The plug 25 is caused to move by a plunger 120 slidably mounted in the casing 102. The plunger 120 includes a semi-cylindrical body 121 with the groove in the front end 122 thereof for insertion into the groove 53 in the plunger 40, whereby the plunger 40 can be pulled out of the syringe body 26 or pushed towards the orifice end thereof. The inner or trailing end of the plunger 120 is defined by a cup-shaped piston 124 sealed in the casing 102 by an O-ring 125. A rod 127 extends rearwardly from the piston 124 into a spring chamber 128, which includes a sleeve 129 surrounding the rod 127. The sleeve 129 includes an annular flange 130 for bearing against a shoulder 131 in the casing 102. The sleeve 129 is retained in position by the externally threaded end 133 of a cylindrical rear end cap 134 of the casing 102. The area between the piston 124 and the sleeve 129 defines a pressure chamber 135, which receives fluid under pressure through an inlet line 137 extending through the handle 103 when (as mentioned above) the trigger 117 is depressed. The fluid comes from a pressure accumulator (not shown) or other source of fluid under pressure. The rod 127, and consequently the piston 124 are biased towards the outer end of the cap 134 by a helical spring 138 sandwiched between the closed inner end 139 of the sleeve 129 and an annular flange 141 on the spring chamber end of the rod 127.

In operation, with the gun in the fired position shown in FIG. 11, the spring 138 moves the rod 139 and the piston 124 away from the orifice end of the injector. Such movement draws the plunger 40 out of the syringe body 26 creating a partial vacuum in front of the second valve 48 (FIG. 8). The vacuum draws medicine into the chamber 39 to fill the chamber. When the trigger 117 is pressed, fluid under pressure is introduced into the pressure chamber 135 via the line 137 to move the plunger 40 rapidly towards the orifice end of the gun. Such movement closes the valve 48 and opens the valve 31. The width of the groove 53 in the plunger 40 is such that there is a gap between the end 122 of the plunger 120 and the orifice end of the groove 53. Thus, as the plunger 120 moves rapidly forwardly it strikes the front end of the groove 53 to discharge a skin piercing drop of medicine through the orifice 30. Thereafter, the plunger 120 pushes the plug 40 forwardly until the medicine has been discharged through the orifice 30. Upon completion of an injection, the chamber 135 is vented, and the spring 138 moves the plunger 120 rearwardly to repeat the syringe filling or loading operation. When the bag carrying the medicine has been emptied, the holder 106 is removed from the neck 105, the syringe 25, the tubing 113 and the bag are discarded. A tube 113 attached to a fresh bag of medicine is inserted through the handle 103 and the slots 114 and 115 into the casing 102, and attached to the tapered end 55 of the plunger 40 of a fresh syringe 25.

I claim:

1. A syringe for a needleless injector comprising tubular body means defining a medicine chamber, said body means having one closed end and an open end; orifice means in said closed end for discharging medicine from said chamber; plug means slidable in said chamber between said open and closed ends for pushing medicine through said orifice means; prong means extending inwardly from said plug means into said means chamber; O-ring means on said prong means for creating a fluid-tight seal between said plug means and said body means; and annular sealing ring means on said prong means for preventing entry of said O-ring means between said plug means and said body means during movement of said plug means towards said orifice means, said sealing ring means including a slot extending through one side thereof facilitating expansion of said ring means against the interior of said body means for preventing movement of said O-ring between said body means and said plug means.

2. A syringe according to claim 1, wherein the end of said ring means nearest to said orifice means is bevelled inwardly for receiving said O-ring means, whereby the pressure of medicine in said chamber forces said O-ring means against the ring means to push the ring means outwardly.

3. A syringe according to claim 1, wherein both ends of said ring means are bevelled inwardly, whereby pressure on either end of the ring means forces the latter outwardly.

4. A syringe according to claim 1, wherein said body means and said lug means are both formed of plastic.

5. A syringe according to claim 1, including first valve means in said body means normally closing said orifice means and adapted to open under the pressure of medicine when said plug means is moved towards said orifice means; passage means in said plug means permitting the introduction of medicine into the chamber between the plug means and orifice means; and second valve means on said prong means normally closing said passage means for opening when said plug means is moved away from said orifice means to create a partial vacuum in said medicine chamber.

6. A syringe according to claim 5, wherein said first valve means includes tube means coaxial with said orifice means extending rearwardly towards said plug means; longitudinal slot means in said tube means; and flexible cap means covering the open inner end of said tube means and extending into said tube means, said cap means normally closing said slot means and flexing under pressure to open said slot means, whereby medicine can be discharged from the chamber.

7. A syringe according to claim 5, wherein said second valve means includes cover means slidable on said prong means for movement between passage opening and closing positions; and stop means on said prong means for limiting movement of said sleeve means between said passage opening and closing positions.

* * * * *